United States Patent [19]
Jenkins et al.

[11] Patent Number: 5,294,457
[45] Date of Patent: Mar. 15, 1994

[54] THERMO-IRREVERSIBLE GEL PARTICLES FOR USE IN FOODS

[75] Inventors: Ronald K. Jenkins; James L. Wild, both of Washington, Pa.

[73] Assignee: Rhone-Poulenc Inc., Monmouth Junction, N.J.

[21] Appl. No.: 901,464

[22] Filed: Jun. 19, 1992

[51] Int. Cl.$^5$ .......................... A23L 1/103; A23L 1/04; A23L 1/317
[52] U.S. Cl. ...................................... 426/573; 426/21; 426/28; 426/31; 426/577; 426/643; 426/644; 426/646
[58] Field of Search ................ 426/573, 643, 21, 644, 426/28, 646, 31, 577, 804

[56] References Cited

U.S. PATENT DOCUMENTS

| | | | |
|---|---|---|---|
| 3,754,925 | 8/1973 | Kimura et al. | 426/135 |
| 4,427,704 | 1/1984 | Cheney et al. | 426/573 |
| 4,582,714 | 4/1986 | Ford et al. | 426/564 |
| 4,647,470 | 3/1987 | Sanderson et al. | 426/573 |
| 4,676,976 | 6/1987 | Toba et al. | 424/485 |
| 4,746,528 | 5/1988 | Prest et al. | 426/805 |
| 4,894,250 | 1/1990 | Musson et al. | 426/573 |
| 4,996,063 | 2/1991 | Inglett et al. | 426/21 |
| 5,011,701 | 4/1991 | Baer et al. | 426/804 |
| 5,082,673 | 1/1992 | Inglett et al. | 426/21 |
| 5,192,569 | 3/1993 | McGinley et al. | 426/804 |

OTHER PUBLICATIONS

Oatrim: Fat reducer, cholesterol fighter. Dean D. Duxbury, Associate Editor Food Processing. Aug. 1990.
Shember Carrageenan Brochure (undated).
Where's the Fat? Latest Ground Beef is 96% Free of It. Richard Gibson. Wall Street Journal, Oct. 3, 1991.
No one fat replacer does it all. National Starch and Chemical Company Food Products Division Brochure (undated).
Oatrim update given by U.S.D.A. at Oatrim Conference on May 18, 1990.
Food Additives. Ann M. Thayer-Chemical and Engineering News, Jun. 15, 1992.
Use of Specialty Food Additives to Continue to Grow. Ann M. Thayer-Chemical and Engineering News, Jun. 3, 1991.

Primary Examiner—Jeanette Hunter
Assistant Examiner—Mary S. Mims
Attorney, Agent, or Firm—Paul J. Juettner

[57] ABSTRACT

A thermo-irreversible gel composition prepared from a soluble dietary fiber which is derived from the amylase hydrolysis of cereal and a hydrocolloid, preferably carrageenan or a blend of xanthan gum and locust bean gum can be effectively used as a fat mimic in preparing low fat comminuted meat products

29 Claims, No Drawings

THERMO-IRREVERSIBLE GEL PARTICLES FOR USE IN FOODS

BACKGROUND OF THE INVENTION

The present invention relates to the provision of thermo-irreversible gel particles for use in foods.

Recently, there has been an extensive emphasis on diet with the goal of reducing caloric and cholesterol intake. One of the major means of accomplishing this goal is the reduction of the intake of fat. Numerous fat mimics products are known and many are available commercially. One such product is an oat based extract patented under U.S. Pat Nos. 4,996,063 and 5,082,673 issued to G. Inglett and identified as Oatrim. This product is the solids portion of the soluble fraction that remains after the partial hydrolysis of oat flour with α-amylase enzyme. The product has a elevated content of β-glucan. In addition to acting as a fat mimic, the product also has the benefit of the known ability of oat soluble fiber and β-glucan to reduce the cholesterol levels in the blood.

While Oatrim has been used in various food systems as a fat mimic or replacer, it has various limitations relative to the area of use. In particular, Oatrim has been added to various ground meat products in order to prepare a reduced fat meat patty or sausage., e.g., frankfurters. However, Oatrim by itself in meat products, while providing good cook yields, provides a meat product that exhibits a weak or mushy texture. In certain processed meat products, definitive fat particles or fat islands are observable within the meat product. While many fat mimics provide the slippery characteristic of fat, most do not lend themselves to the formation of fat mimic particles which are stable at the heating or cooking temperatures of the meat product. Sausages such as kielbasy, pepperoni and salami rely on the fat particles for appearance, taste and mouth feel. These fat particles are recognized by the consumer as an essential part of the product. In order to provide a fat reduced sausage of this type, it will be necessary to substitute the fat particles with non-fat particles which can provide the taste and mouth feel of the original product and which can withstand the processing temperatures and cooking conditions (smoking, boiling, baking, and barbecuing) applied to these products. Oatrim as presently constituted cannot be used effectively to provide fat mimic particles satisfying these characteristics and conditions.

It has been discovered that thermo-irreversible gels can be prepared using Oatrim as the base which withstand the heating and cooking needed to provide that type of product while providing the visual, taste and mouth feel characteristics desired in a fat mimic particle for meat products.

SUMMARY OF THE INVENTION

In accordance with the invention, water soluble dietary fiber compositions can be made into thermo-irreversible gels by the process of the invention. These gels can be mixed with food to effect a replacement of fat or other ingredients or act as a filler or flavor carrier or decoration. Particularly, the gels can be used as fat mimics in combination with communicated meats in such products as sausages.

The claimed process includes the steps of blending soluble dietary fiber compositions, also described as soluble cereal hydrolysates, as defined hereinafter with a hydrocolloid capable of forming a thermo-irreversible gel as defined herein.

DETAILED DESCRIPTION OF THE INVENTION

As used herein, the term "Oatrim" is intended to specifically refer to the solids recovered from the water soluble fraction after separating the soluble fraction from the insoluble fraction by partial amylase hydrolysis of oat flour as defined herein.

Broadly, the term "soluble cereal hydrolysate" is intended to cover the solids from the soluble fraction prepared as defined above using the cereals as listed hereinafter.

The soluble cereal hydrolysate used in the invention, i.e., the soluble dietary fiber material, can be formed using the process of U.S. Pat. Nos. 4,996,063 and 5,082,673, the disclosures of which are incorporated herein by reference.

The term "thermo-irreversible gel" as used herein is intended to mean a gel which substantially retains its shape and integrity in the system in which it is used after heating the system to a temperature of 71° C. (160° F.) for 15 minutes.

Suitable substrates contemplated for use in preparing the hydrolysates used in the invention include cereal flours, milled cereal brans, cereal starches, tuber starches, and blends thereof. Of particular interest are the whole flours of barley, oats, wheat, corn, rice, rye, triticale, and milo, as well as the flours prepared from bran or other fractions of the milled grain. Preferably, the substrate is whole oat flour.

The substrate is slurried in a sufficient amount of water to give a concentration in the range of about 10–40% by weight. The water can contain a suitable calcium content in an amount sufficient to stabilize the subsequently added α-amylase, such as about 25–50 part per million (ppm) of calcium. The slurried substrate may be gelatinized prior to enzymatic treatment, using any method known in the art such as heating. The pH of the ungelatinized slurry or the gelatinized dispersion can be adjusted to about 5.5–7.5, preferably about 6.0, with appropriate acid or base addition, i.e., sodium hydroxide or other alkali.

It is advantageous to use thermostable α-amylases referred to as 1.4-α-D-glucan glucanohydrolases and having the essential enzymatic characteristics of those produced by the Bacillus stearothermophilus strains ATCC Nos. 31,195; 31,196; 31,197; 31,198; 31,199; and 31,783. These strains are described in U.S. Pat. No. 4,284,722 which is incorporated herein by reference. Other sources of this enzyme include organisms as B. subtilis which have been genetically modified to express the thermostable α-amylase of B. stearothermophilus as described in U.S. Pat. No. 4,493,893 incorporated herein by reference. These enzymes are available commercially under the name "G-zyme G995" (formerly called "Enzeco Thermolase"; Enzyme Development Div., Biddle Sawyer Corp., New York, N.Y.)

Other suitable α-amylases are those produced by B. licheniformis var. as described in U.S. Pat. Nos. 4,717,662 and 4,724,208, herein incorporated by reference. These enzymes are available commercially under the name "Taka-Therm L-340" (formerly called "Takalite" Solvay Enzyme Products, Inc., Elkart, Inc.). Of course, any α-amylase which is useful in the thinning of the starch is contemplated for use herein.

The conditions of enzyme treatment, including the enzyme concentration and the time and temperature of reaction, are selected to achieve liquefaction of the starch in the substrate. When using a thermostable α-amylase, a preferred treatment temperature is in the range of 70°–100° C., preferably about 95° C. At these temperatures, gelatinization of the starch in the substrate occurs concurrently with the hydrolysis. The duration of the treatment at the desired conversion temperature depends on the desired product properties and will generally range from about 2–60 min.

After completion of the enzymatic hydrolysis, the enzyme is inactivated, such as by passing the mixture through a steam injection pressure cooker at a temperature of about 140° C. Alternatively, the enzyme may be inactivated by acidification, such as at a pH 3.5–4.0 at 95° C. for about 10 min. A combination of these methods can also be used. Optional neutralization with alkali increases the salt concentration of the product and this could be less desirable. A natural pH product can be made by avoiding the acid enzyme inactivation step and relying solely on heat inactivation. After the enzyme has been inactivated, the soluble fraction comprising the soluble dietary fiber and the maltodextrins (maltooligosaccharides) is separated from the insoluble residue by any appropriate means such as by centrifugation of the hydrolysates. In a preferred embodiment of the invention, temperatures during centrifugation are maintained less than 70° C., and most preferably within the range of 5°–50° C. Under these conditions of separation, the levels of lipids and proteins in the dietary fiber products are significantly reduced. Water is then removed from the soluble fraction by any of a variety of conventional techniques, whereby the products of this invention comprising the dietary fiber and maltodextrins are recovered. The maltodextrins produced by the process of the invention have a D.E. of 20 or less. These maltodextrins are substantially water soluble at elevated temperatures (e.g., 70°–100° C.)

The soluble dietary fiber recovered from the centrifugate is principally in the form of β-glucans and pentosans. Of course the relative amount of each fiber type varies with the species of substrate. Oat and barley substrates yield mostly the β-glucans; whereas wheat, rice, and corn yield the pentosans.

Representative Method of Preparing Soluble Oat Fiber in accordance with Example 10 of U.S. Pat No. 5,082,673

Six kilograms of oat flour can be slurred in 18 liters of water containing 25 ppm of calcium. The pH of the slurry was 5.75. After gelatinization by passage of the mixture through a steam injection cooker, the slurry can be collected in a 30 gallon (113.5 liter) steam-heated cooker. Alpha amylase can then be added to the slurry in an amount sufficient to provide 1 unit per gram of oat flour. After 5 minutes of stirring at 80°–90° C., the enzyme can be inactivated by passing the slurry through a steam injection cooker. The warm slurry can be centrifuged at 15,000 rpm by a large "Sharples" centrifuge to separate the soluble and insoluble components. The products can be dried separately on hot rolls. The oligomer composition can be 98% DP 9 and larger.

The hydrocolloids for use in the invention include carrageenan (kappa or iota) or a mixture of xanthan and locust bean gum. Preferably, the hydrocolloid is kappa (κ) carrageenan. Effective ratios of xanthan to locust bean depend on use area (e.g. 4:1 to 1:4) preferably 1:1.

The soluble dietary fiber composition/hydrocolloid gel can be prepared by blending the water soluble dietary fiber composition and the hydrocolloid in water until the substrate is swollen and the gum is dissolved and well mixed. It has been found that room temperature water can be used to manufacture the gels by blending the ingredients in a planetary mixer along with the room temperature water. Hot (75°–100° C.) water can also be used if desired. After cooling, such as in a refrigerator over night, the gel is set. The gel is usually comminuted to small pieces such as within the range of from about 0.1 centimeters (0.04 inches) to about 1.3 centimeters (0.5 inches). The gel can be stored in a cool place until needed to prevent bacteriological degradation. The gel can be prepared with coloring, flavors, preservatives, protein enhancers, fillers and the like. The gel can be used chopped or in shaped particles.

The water soluble dietary fiber is used in a ratio to the hydrocolloid of from about 80–88 parts hydrolysate to from about 20 to about 12 hydrocolloid, preferably from about 88 to about 86 parts to from about 18 to about 14 parts and more preferably from about 83 to about 85 parts to from about 17 to about 15 parts. Most preferably, the cereal hydrolysate is used in an amount of 84 parts hydrolysate to 16 parts hydrocolloid. The blend of xanthan gum and locust bean gum would be considered a hydrocolloid for these ratios.

The gel is added to the comminuted meat in an amount as needed to provide the effect needed. In general, the gel can be used in an amount ranging from about 4% to about 30%. The amount of gel which can be used as a fat mimic depends on the area of use. As used herein, comminuted meat is intended to cover meat muscle which has been interrupted from its natural form such as by cutting, shredding, chopping, grinding, emulsifying and the like. The comminuted meat pieces preferably have a size of less than 2.5 centimeters (1 inch) and more preferably less than 0.6 centimeters (0.25 inch). Appropriate particle sizes for products such as patties and sausages are well known to the skilled artisan.

The comminuted meat may be derived from any usual meat source using any conventional recipe [such as from bovine (cow, bull, steer, calf), sheep (lamb and mutton), swine (pigs, hogs), wild game (elk, deer) and fowl (chicken, turkey, duck, goose)] and conventional preparation techniques such as disclosed in "Sausage and Processed Meats Manufacturing, Robert E. Rust, AMI Center for Continuing Education, American Meat Institute (1977), which is incorporated herein by reference.

The comminuted meat can include conventional ingredients such as curing agents and preservatives, spices, and flavor accentuators, fillers, coloring, and the like. These can be illustrated by alkali metal chlorides, nitrites, nitrates, phosphates (pyro and poly), sorbates, benzoates, erythorbates, citrates and citric acid, sugar and sugar derivatives, cereal flour and cereal derivatives, spices and spice extracts, oleo resins, seasonings, flavors, curing adjuncts such as glutamic acid and GDL, fats, oils, modified fats and oils, solvents such as water, alcohol or glycerin, vitamins, amino acids, proteins (natural, hydrolyzed, modified, isolated), flavor enhancers such as MSG or soy sauce, smoke flavorings, coloring agents such as paprika, tomato pumice, beet extract, artificial colors and the like as desired.

The comminuted meat products can be in the form of patties, sausage (pork, bologna), cooked and fermented sausage (salami and pepperoni), frankfurters (hot dogs) and the like products either formed or in casings. Sectioned and formed products are also included in the term comminuted products.

The following examples are presented only to further illustrate the invention and are not inserted to limit the scope of the invention which is defined by the claims. All percentages are by weight unless otherwise stated.

EXAMPLE 1

Materials and Formulations

The Oatrim used in the following example was prepared by admixing at room temperature sufficient whole oat flour with water containing calcium to provide a slurry of about 25% solids by weight. The pH of the slurry is 6.2. Taka-therm enzyme in the amount equivalent to 0.7 grams per kilogram of total solids was added. The enzymatic hydrolysis was allowed to proceed at 92°–95° C. for a retention time of 1.5–2 minutes. The pH was then adjusted to pH 4 with phosphoric acid and heated to 130° C. for six minutes in order inactivate the enzyme. The pH was then adjusted to 5.5 with caustic and the material was centrifuged to separate the insoluble solids from the mother liquor. The mother liquor was dried in a drum dryer to provide the Oatrim product which had a pH of 5.3, a viscosity of 58 centipose (5% solution using spindle #3) and a moisture content of 6.7%.

Of the fat mimics used in this Example, three were preformed gels. These included:

| 1. & 2. | Mimic-I [Iota] (Gel) or Mimic-III [Kappa] (Gel) | |
|---|---|---|
| | a. Oatrim | 21% |
| | b. Kappa Carrageenan or Iota Carrageenan | 4% |
| | c. Water | 75% |
| 3. | Mimic II [Oatrim/Xanthan Gum/Locust Bean Gum] (Gel) | |
| | a. Oatrim | 21% |
| | b. Xanthan Gum (dispersible) | 2% |
| | c. Locust Bean Gum | 2% |
| | d. Water | 75% |

Process for Preparing Gels

After boiling the water, weighing and mixing the dry ingredients, and calibrating a food processor bowl (Cuisinart) to 375 grams of liquid, the boiling water was poured into the food processor bowl up to the previously calibrated 375 gram level. The temperature immediately after pouring was recorded, specification is 90° C. or higher. With the food processor blades in operation, the dry ingredients were rapidly blended into the water, mixing for one minute on low speed. The resultant slurry/gel was removed to a sealable container (beaker) and placed in cooler 0° C.–3.3° C. (32°–38° F.) overnight to set the gel.

Three dry blends were also prepared:

| 1. Mimic-III (Dry) | | |
|---|---|---|
| | a. Oatrim | 84% |
| | b. Kappa Carrageenan | 16% |
| 2. Mimic-I (Dry) | | |
| | a. Oatrim | 84% |
| | b. Iota Carrageenan | 16% |
| 3. Mimic II (Dry) | | |
| | a. Oatrim | 84% |
| | b. Xanthan (Dispersible) | 8% |
| | c. Locust Bean Gum | 8% |

Meat Mixture Composition

With the exception of the 30% fat control, the base formulation contained the following:

| Pork Trim | 21.63% | |
|---|---|---|
| Beef Round | 3.14% | |
| Pork Picnic | 38.25% | |
| Water | (32.50% - | Dry Fat Replacer) + 10% Added Water |
| Fat Mimic | See Table I. | |
| Spice (Includes Salt) | 4.40% | |
| Sodium Erythorbate | (0.06%) | |
| Sodium Nitrite | (0.02%) | |

Each low-fat formulation was prepared to contain 239.5 bind units (U. Georgia, College of Agriculture) and 9.5% fat content as per guidelines of a low-fat frankfurter formulation. Treatment addition levels of the various fat mimic ingredients are listed in Table I.

The 30% fat control contained:

| Pork Trim | 11.52% |
|---|---|
| Pork back fat | 24.00% |
| Beef Round | 11.00% |
| Pork Picnic | 34.00% |
| Water | 15.00% |
| Spice (+ salt) | 4.40% |
| Sodium Erythorbate | 0.067% |
| Sodium Nitrite | 0.02% |

Meat Mixture Preparation

For each treatment, separate meat blocks were prepared according to the base formulation previously described. Prior to chopping in a food processor (Cuisinart), the treatment formulation was blended using a Hobart planetary mixer according to the following procedures:

1. Meat block components were mixed for 30 seconds at slow (#1) speed.
2. The spice blend including the salt and sodium erythorbate were added and mixed for an additional 30 seconds at the #1 setting.
3. Ice water and the dry fat replacer ingredients (if applicable) were added and mixed for 60 seconds at the #1 speed setting.
4. Pre-dissolved sodium nitrite was added and mixed for a final 30 seconds.
5. From each of the mixed meat blocks, five 1000 gram units were removed and assigned to each of five chopping times at 0, 1, 2, 3, 4, and 5 minutes.
6. In the 4 treatments using the preformed gel, only water was added in Step 3. The gels, pre-chopped by hand (knife), were added (140 grams) to an 860 gram mixed meat block immediately prior to food processor chopping in Step 7.
7. The 1000 gram units were then chopped for 0, 1, 2, 3 or 4 minutes using a food processor (Cuisinart Model DLC-7). Temperatures of the mixture following chopping were recorded. The sides of the food processor bowl were scraped every minute to insure a more homogeneous mixture.

8. Each treatment was then placed into two aluminum loaf pans. A vacuum was not drawn to eliminate air pockets as the formulations were very fluid.

9. Each loaf pan was weighed and then crimp covered with aluminum foil. All loaves were then kept at 1.1° C. (34° F.) overnight prior to smokehouse cooking.

Cooking Procedure

Following the overnight chilling, the loaves were smokehouse cooked 2.5 hours at a wet bulb/dry bulb temperature of 76.6°/60° C. (170°/140° F.) until an internal temperature of 71° C. (160° F.) was reached and maintained for at least 15 minutes. The loaves were kept in an unheated smokehouse for 1.5 hours after which each loaf was weighed and the cook purge drawn off and volumetrically measured. Each loaf was then placed into a plastic pouch and held at 1.1° C. (34° F.) until needed for organoleptic appraisal.

The loaves were stored at 1.1° C. (34° F.) for 5 days prior to sensory evaluation. The 4 minute chop series of the treatment samples were then evaluated for texture, flavor and visual quality. It was found that even after cooking, the gel particles of Mimics-I, II and III (Gel) were still intact and visually discernable in the meat product structure. The product gave an attractive sausage appearance and mouth feel and taste even though the fat content had been reduced by 20% over the 30% fat in the normal product.

TABLE I

| AVERAGE COOK YIELD (%) BY CHOP TIME IN MINUTES | | | | | |
|---|---|---|---|---|---|
| | 0 | 1 | 2 | 3 | 4 |
| Mimic-III (Gel) 14% | 84.80 | 93.80 | 94.80 | 94.40 | 92.90 |
| Mimic-I (Gel) 14% | 85.10 | 92.10 | 90.03 | 86.10 | 84.70 |
| Mimic-II (Gel) 14% | 86.10 | 96.00 | 95.90 | 96.10 | 95.60 |
| Mimic-III (Dry) 3.5% | 68.70 | 86.50 | 89.30 | 89.70 | 88.40 |
| Mimic-I (Dry) 2.5% | 67.30 | 84.10 | 85.50 | 86.20 | 83.30 |
| Mimic-I (Dry) 3.5% | 69.30 | 83.90 | 86.30 | 87.90 | 86.70 |
| Mimic-II (Dry) 3.5% | — | 95.00 | 93.40 | 94.20 | 94.60 |
| CONTROL SAMPLES | | | | | |
| Control (10% Fat) | 67.77 | 81.19 | 85.09 | 86.81 | 85.67 |
| Control (30% Fat) | 82.91 | 91.18 | 81.22 | 76.37 | 70.64 |
| Oatrim (3.5%) | 66.21 | 76.59 | 79.69 | 80.63 | 77.79 |
| Oatrim (2.5%) | 63.10 | 75.60 | 81.60 | 81.30 | 80.60 |
| Rice-trin (3.5%) | 67.60 | 74.40 | 76.40 | 77.20 | 76.20 |
| Carrageenan-Kappa (0.5%) | | | | | |
| Source 1. | 80.00 | 90.2 | 92.60 | 93.70 | 94.00 |
| Source 2. | 82.00 | 92.10 | 93.5 | 95.00 | 93.80 |
| Oat Bran (3.5%) | 84.80 | 93.30 | 94.10 | 94.40 | 94.20 |

RESULTS

Cook Yields

Cook yields by formulation and chop time are summarized in Table I. Of the fat mimics evaluated, the highest cook yields and the greatest stability to overchop stress (no yield loss over length of chop) were attained with the dry and gel forms of Mimic-II and Mimic-III blends.

Gels of Mimic-II and Mimic-III provided higher cook yields than the dry counterparts. The differences between the two forms of Mimic-III were pronounced whereas the differences between the two versions of Mimic-II were small. The yields for Mimic-I were lower and could indicate that this gel form is not resistant to high shear.

ORGANOLEPTIC and VISUAL APPRAISAL

Informal organoleptic evaluations were conducted on the 4 minute chop series.

TEXTURE

The texture of the 30% fat control appeared dry, firm, and chewy as compared to the softer, smoother texture of the low-fat control. Of the low-fat formulations, the low-fat control, both carrageenan treatments, the oat bran and the dry application of Mimic-II and Mimic-I provided the firmest products. The Oatrim and Rice-trin only treatments provided meat products which appeared dry and mealy.

FLAVOR

With the exception of the a slight bitterness detected with the carrageenan from Source 1., the flavor of the various fat mimic gels was considered acceptable. Primary differences between treatments appeared to be based on the intensities of spices, sugar and smoke flavor perception. Those treatments containing either Mimic-I or Mimic-III appeared to be sweeter than other treatments.

VISUAL APPRAISAL

Many air pockets were present throughout the cooked products due to the inability of a vacuum treatment to lower the residual air. Except for Mimic-III and Mimic-II gel systems, the low fat loaves were similar in appearance. Small gel particles were visible in the Mimic-II and Mimic-III chop series. It appears that the fine gel particles remaining following chopping continued to hydrate during the subsequent dwell and cook processes. With such additional hydration, the swollen gel particles thus appeared visible in the cooked matrix.

While, of the single ingredient systems, both kappa carrageenan and oat bran provided the highest cook yields and chop stabilities, the gel and dry forms of Mimic-II and Mimic-III provided the highest cook yields and chop stabilities along with the benefits of the soluble dietary fiber product. This is in contrast to Oatrim only treatments which provided only a measure of chop stability, and cook yields were lower than that of the low-fat (10%) fat control.

With the possible exception of the Oatrim and Rice-trin formulations which appeared dry and mealy, none of the low-fat treatments exhibited a negative textural state. Flavors were acceptable for the products of the invention.

EXAMPLE 2

The Oatrim utilized in preparing the Mimic-III (gel) in the following example was prepared by admixing sufficient whole oat flour at room temperature with a pre-determined amount of calcium containing (100 ppm) water to provide a slurry of 20% solids by weight. Taka-therm enzyme was added to the slurry in an amount of 1.0 grams per kilogram of total solids diluted with 19.6 grams of water. The enzymatic hydrolysis was allowed to proceed at 90° C. for two minutes in a pressure cooker. The enzyme was inactivated by cooking in a pressure cooker at 131° C. The slurry was flashed to release excess vapor and odor. After removing the insoluble portion by centrifugation, the mother liquor was dried in a drum dryer. The product had a viscosity at a 5% solution of 88 centipose (using spindle #3), pH of 6.29 and a moisture content of 3.9%.

To study the efficacy of using a firm thermally stable gel as a fat replacer in a course-cut sausage product, a fat reduced kielbasa was prepared containing a fat particle look-alike comprised of Mimic-III (gel). The gel, prepared using a Hobart planetary mixer (speed #2) and boiling water (mixed 1 minute), consisted of 75 parts water and 25 parts of dry Mimic-III (84 parts Oatrim and 16 parts kappa carrageenan). Formulations for the standard high fat (30%) kielbasy and a reduced fat (10%) version containing the Mimic-III (gel) are listed below in Table IV.

TABLE IV

| Ingredients | Ingredient % | |
| --- | --- | --- |
| | Hi Fat Control | Mimic-III (gel) |
| Fresh Ham | 40.51 | 45.38 |
| Beef (90/10 trim) | 15.51 | 12.51 |
| Pork Back fat | 21.55 | 4.67 |
| Water | 17.5 | 20.0 |
| Mimic-III (gel) | — | 12.5 |
| Spice and Salt | 4.5 | 4.5 |
| Phosphate | 0.4 | 0.4 |
| Nitrite | 0.01 | 0.01 |
| Erythorbate | 0.03 | 0.03 |

The smokehouse cook yields for the high fat control and Mimic-III treatment were identical (79%). Although the kielbasy was not tested by a formal panel, at least a dozen staff members tasted the product in both a cooked, chilled and a reheated state. The remarks were consistent with the reduced fat Mimic-III product closely resembling the high fat control sample. The visible gel particles resembled the characteristic visible fat particles in the high fat standard product. The Mimic-III (gel) pieces provided a mouth feel similar to that of the fat particles in the high fat standard. The texture of the reduced fat product was slightly firmer but still considered highly acceptable.

The use of Mimic-III (gel) in pepperoni is currently being tested. Preliminary results indicate that the pepperoni has a desirable flavor texture and mouth feel. The simulated fat particles (i.e, Mimic-III (gel)) exhibited fat like characteristics during grinding and further processing (stuffing, etc.).

The fat mimics as used in these examples could be prepared using the same process but at different times.

It is understood that the foregoing description is given merely by way of illustration and that modification and variations may be made therein without departing from the spirit and scope of the invention.

What is claimed is:

1. A thermo-irreversible gel comprising
   A. a water soluble dietary fiber material from cereals prepared by hydrolyzing an aqueous dispersion of a cereal substrate with an amylase enzyme under conditions which will hydrolyse the starch without appreciable solubilization of the substrate protein to yield water soluble and insoluble fractions, isolating the soluble fraction, and separating the water soluble dietary fiber from said soluble fraction, and
   B. a hydrocolloid effective and in an amount sufficient to form a thermo-irreversible gel with said water soluble dietary fiber.
2. The composition as recited in claim 1 wherein said cereal substrate dispersion is in the range of about 10–40% solids.
3. The composition as recited in claim 1 wherein said cereal substrate comprises a flour selected from the group of oats, barley, wheat, corn, rice, rye, triticale, and milo from barley.
4. The composition as recited in claim 3 wherein said cereal substrate is oat flour.
5. The composition as recited in claim 3 wherein said cereal substrate is barley flour.
6. The composition as recited in claim 1 wherein the α-amylase and the cereal substrate are gelatinized concurrently with the hydrolysis by treating the substrate with the amylase enzyme at a temperature in the range of about 70°–100° C.
7. The composition as recited as in claim 1 wherein step (b) of separating the soluble fraction from the insoluble fraction is conducted by centrifugation at a temperature less than about 70° C.
8. A composition is recited in claim 1 wherein the water soluble dietary fiber material is used in proportion to the hydrocolloid in a range from about 80 to about 88 parts water soluble dietary fiber material to about 20 to about 12 parts hydrocolloid.
9. A composition is recited in claim 1 wherein the water soluble dietary fiber material is used in proportion to the hydrocolloid in a range from about 80 to about 86 parts water soluble dietary fiber material to about 18 to about 14 parts hydrocolloid.
10. A composition is recited in claim 1 wherein the water soluble dietary fiber material is used in proportion to the hydrocolloid in a range from about 83 to about 85 parts water soluble dietary fiber material to about 17 to about 15 parts hydrocolloid.
11. A composition is recited in claim 1 wherein about 84 parts of water soluble dietary fiber material is used to about 16 parts of hydrocolloid gum.
12. A food composition comprising
   A. a dietary fiber product produced by the method of
      a. Hydrolyzing a cereal substrate with an amylase enzyme under conditions which will hydrolyze the starch without appreciable solubilization of the substrate protein to yield water soluble and insoluble fractions, and
      b. Isolating the soluble fraction and recovering from said soluble fraction said dietary fiber product;
   B. a hydrocolloid gum effective to form a thermol-irreversible gel with said water soluble dietary fiber, and
   C. one or more digestible food components.
13. A food composition comprising a dietary fiber product produced by the method of:
   a. treating an aqueous dispersion of a milled, cereal substrate with an α-amylase under conditions which will hydrolyze the substrate starch without appreciable solubilization of the substrate protein and thereby yield a soluble fraction and an insoluble fraction;
   b. separating said soluble fraction from said insoluble fraction under conditions which minimize the level of protein in the soluble fraction;
   c. recovering from said soluble fraction said water-soluble dietary fiber substantially free of water insoluble fiber; and
   d. combining said water-soluble dietary fiber with a hydrocolloid effective and in an amount sufficient to form a thermo-irreversible gel with said water soluble dietary fiber, and
   e. combining the water-soluble dietary fiber gel from step (d) with one or more digestible food components.

14. A food composition as recited in claim 13 wherein said cereal substrate comprises a flour selected from the group of oats, barley, wheat, corn, rice, rye, triticale, and milo.

15. A food composition as recited in claim 13 wherein said cereal substrate is oat flour.

16. A food composition as recited in claim 13 wherein said cereal substrate is oat bran.

17. A food composition as recited in claim 13 wherein said cereal substrate is barley flour.

18. A food composition as recited in claim 13 wherein said food component is a comminuted meat.

19. A food composition as recited in claim 18 wherein said comminuted meat is derived from bovines, sheep, swine and fowl.

20. A food composition as recited in claim 18 wherein said comminuted meat is sausage.

21. A food composition as recited in claim 13 wherein said hydrocolloid is selected from the group consisting of carrageenan and a mixture of xanthan gum and locust bean gum.

22. A food composition as recited in claim 13 wherein said hydrocolloid is x-carrageenan.

23. A food composition as recited in claim 13 wherein said hydrocolloid is a blend of xanthan gum and locust bean gum.

24. A food composition is recited in claim 13 wherein the water soluble dietary fiber material is used in proportion to the hydrocolloid in a range from about 80 to about 86 parts water soluble dietary fiber material to about 18 to about 14 parts hydrocolloid.

25. A food composition is recited in claim 13 wherein the water soluble dietary fiber material is used in proportion to the hydrocolloid in a range from about 83 to about 85 parts water soluble dietary fiber material to about 17 to about 15 parts hydrocolloid.

26. A food composition is recited in claim 13 wherein about 84 parts of water soluble dietary fiber material is used to about 16 parts of hydrocolloid gum.

27. A food composition as recited in claim 12 wherein said food components are comminuted meat.

28. A thermo-irreversible gel as recited in claim 1 wherein said hydrocolloid is x-carrageenan.

29. A thermo-irreversible gel as recited in claim 1 wherein said hydrocolloid is a blend of xanthan gum and locust bean gum.

* * * * *